United States Patent [19]

Erbel

[11] Patent Number: 5,436,211
[45] Date of Patent: Jul. 25, 1995

[54] PROCESS FOR THE RECOVERY OF ADSORBED SOLVENTS

[75] Inventor: Horst Erbel, Augsburg, Germany

[73] Assignee: Pero KG, Konigsbrunn, Germany

[21] Appl. No.: 978,707

[22] PCT Filed: Jun. 6, 1992

[86] PCT No.: PCT/EP92/01283
   § 371 Date: Feb. 2, 1993
   § 102(e) Date: Feb. 2, 1993

[87] PCT Pub. No.: WO93/00151
   PCT Pub. Date: Jan. 7, 1993

[30] Foreign Application Priority Data

Jun. 29, 1991 [DE] Germany .................. 41 21 697.0

[51] Int. Cl.[6] .................... B01J 20/34; B01J 38/04
[52] U.S. Cl. .................... 502/56; 502/20;
      502/34; 203/58; 203/67; 570/262
[58] Field of Search .............. 502/56, 20, 34; 34/15;
      203/91, 58, 67; 202/164; 570/262

[56] References Cited

U.S. PATENT DOCUMENTS 3,396,473  8/1968  Turner ..................... 502/56
4,621,437 11/1986  Grande et al. ............. 34/15
5,187,131  2/1993  Tigglebeck et al. ......... 502/56

Primary Examiner—Anthony McFarlane
Attorney, Agent, or Firm—Pascal & Associates

[57] ABSTRACT

The invention concerns a process for the recovery of a solvent adsorbed in an adsorber, or other substances which are condensable. The adsorber (3) is, at first, heated to a temperature which is below the decomposition temperature of the solvent, then the adsorber chamber (2) is sealed off from the surroundings and a high negative pressure is applied to the adsorber chamber (2), as a result of which the solvent is desorbed. During a portion of the time when this high negative pressure is applied, the temperature of the adsorber (3) is brought to a value which is above the decomposition temperature of the solvent. In spite of this, there is no decomposition under the noted conditions, however, the high temperature does enable an almost complete desorption of the solvent. Finally, the desorbed solvent is drawn off from the adsorber chamber (2) and condensed.

12 Claims, 1 Drawing Sheet

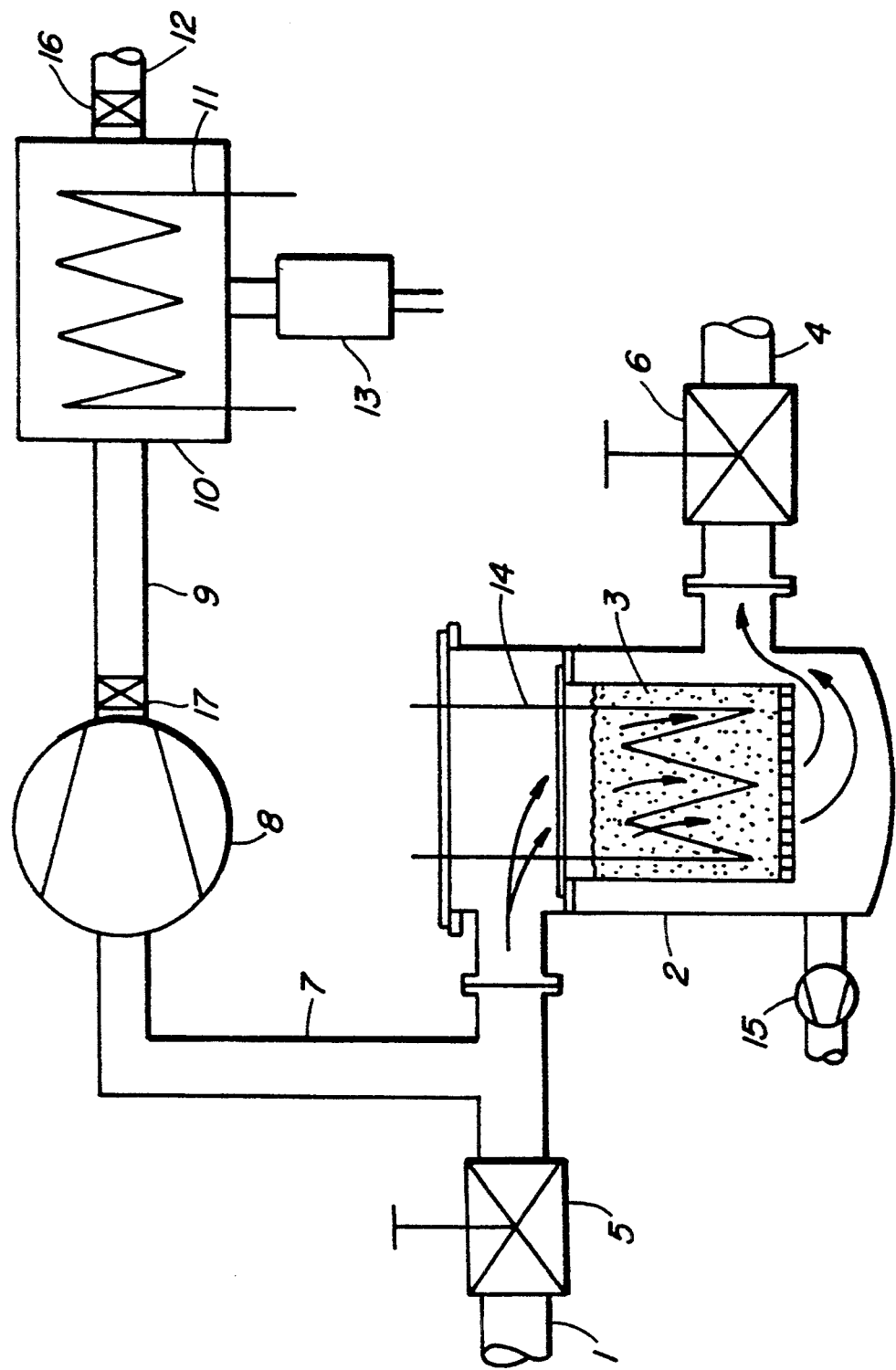

PROCESS FOR THE RECOVERY OF ADSORBED SOLVENTS

FIELD OF THE INVENTION

The invention concerns a process for the recovery of polluting substances adsorbed in an adsorber such as, for example, solvents.

BACKGROUND OF THE INVENTION

DE PS 30 48 649 describes a process for the recovery of halogenated hydrocarbons adsorbed in activated carbon. In this process, hot air flows through the activated carbon, whereby the adsorbed hydrocarbons are desorbed and pass over into the air flowing through. The air flowing off is then cool ed, which results in a condensation of the hydrocarbons dissolved therein. By again heating and returning the air to the activated carbon, this procedure can be repeated several times. However, strict attention must always be paid to the fact that the temperature of the air remain below the decomposition temperature of the halogenated hydrocarbons. The upper limit for the temperature of the hot air flowing through is, for example, 120° C. with trichloroethylene and 150° C. with perchloroethylene. These values apply to normal atmospheric surroundings. Atmospheric pressure of about 1000 mbar can thereby be considered to be normal atmospheric pressure.

The disadvantage of this process is that, in spite of repeating the procedure several times, there is no complete desorption of the hydrocarbons from the activated carbon filter. In addition, the air has a residue of hydrocarbons after the process has been completed.

Other embodiments of this process are published in the Patent Abstracts of Japan, Unexamined Applications, Section C, Volume 2, No. 59, 27. April 1978, page 458 C 78, No. 53-18504 and in EP 0 381 942. In these publications, the desorption of the adsorbed hydrocarbons is promoted by applying a negative pressure to the adsorber chamber. In EP 0 381 942, the adsorber is first heated to a temperature which is below the decomposition temperature of the adsorbed substance, the adsorber chamber is then sealed off from the surroundings and a high negative pressure is applied. Finally, the desorbed substance is drawn off from the adsorber chamber and the temperature and pressure ratios set in such a way that it condenses.

This process, which is promoted by negative pressure, is in fact superior to the first process mentioned. However, it also does not enable a complete desorption since the maximum working temperature is again limited by the decomposition temperature of the adsorbed substance. Using higher temperatures, at which a substantially improved desorption would take place, is thus not possible.

SUMMARY OF THE INVENTION

Thus, it is the object of the invention to develop the process in such a way that an almost complete desorption of the adsorbed substance is made possible.

In accordance with an embodiment of the invention, a process for the recovery of solvents adsorbed in an adsorber, is comprised of procedural steps of heating the adsorber to a temperature which is below the decomposition temperature of the solvent, sealing the adsorber chamber off from the surroundings, applying a high negative pressure to the adsorber chamber, drawing the desorbed solvent off from the adsorber chamber, and condensing the desorbed solvent by cooling at a suitable pressure characterized therein that the temperature of the adsorber is increased to above the decomposition temperature of the solvent (at normal atmospheric pressure) during at least a portion of the time when the high negative pressure is applied to the adsorber chamber.

In accordance with an embodiment, more particularly, a process for the recovery of solvents adsorbed in an adsorber is comprised of the steps of heating the adsorber in an adsorber chamber to a temperature which is below the decomposition temperature of the solvent, coating the adsorber chamber off from the surroundings, applying a high negative pressure below the value of 10 m bar to the adsorber chamber, drawing the desorbed solvent off from the adsorber chamber, condensing the desorbed solvent by cooling at a suitable pressure, and increasing the temperature of the adsorber to above the decomposition temperature of the solvent (at normal atmospheric pressure) for an effective period during at least a portion of the time when the high negative pressure is applied to the adsorber chamber.

BRIEF DESCRIPTION OF THE DRAWINGS

A better understanding of the invention will be obtained by referring to the detailed description below of a preferred embodiment of the invention, with reference to the single drawing, which is a schematic illustration of an apparatus used to carry out the preferred embodiment of the invention.

DETAILED DESCRIPTION OF THE PREFERRED EMBODIMENT OF THE INVENTION

With reference to the drawings, air mixed with an organic solvent, such as e.g. trichloroethylene, perchloroethylene or trichloroethane, reaches the container 2 in which the adsorber 3, e.g. an activated carbon filter, is found, via pipe 1. After having passed through the adsorber 3, the cleaned air leaves it via pipe 4. The pipes 1 and 4 each have a slide valve 5, 6. Pipe 1 has a branch to a pipe 7 which leads to a vacuum pump 8. A cooling system which consists of a cooling tank 10 and a cooler 11, and which also has a separator 13, is located on the other side of this vacuum pump. A heating device 14 is located in the adsorber 3.

When the adsorber 3 is enriched with solvent, then it no longer has a filtering function and must be desorbed. To accomplish this, it is heated to a temperature which is, at first, below the decomposition temperature of the adsorbed substance. The adsorber chamber is then evacuated via the vacuum pump 8, which promotes desorption in a known manner. The typical residual pressure in the adsorber chamber is 10 to 100 mbar.

EXAMPLE

According to the invention, the temperature of the adsorber 3 can now be increased to values above the decomposition temperature of the solvent by reducing the pressure further to under 1 mbar, without the solvent decomposing. This is a decidedly surprising effect. Experts in the field have thusfar considered the decomposition temperature of the solvent to be the absolute upper limit for heating.

In a successful experiment temperatures up to just under 300° C. have been set up, without the expected decomposition taking place. Using such high temperatures produced an almost complete desorption of the solvent from the adsorber 3 due to the thermal excitation of the solvent molecules.

Subsequent to this high-temperature phase, it is again cooled and the desorbed substance drawn off from the adsorber chamber 2. Cooling the desorbed substance to at least a temperature at which the substance condenses and with a renewed increased pressure takes place in a known manner and is described in EP 0 281 941.

The process for the recovery of solvents adsorbed in an adsorber thus is comprissed of the steps of heating the adsorber to a temperature which is below the decomposition temperature of the solvent, sealing the adsorber chamber off from the surroundings, applying a high negative pressure to the adsorber chamber, drawing the desorbed solvent off from the adsorber chamber and condensing the desorbed solvent by cooling at a suitable pressure, the temperature of the adsorber being increased to above the decomposition temperature of the solvent (at normal atmospheric pressure) during at least a portion of the time when the high negative pressure is applied to the adsorber chamber.

Preferably, the adsorber is first cooled to a temperature which is below the freezing point of the solvent, and during the subsequent increase in temperature of the absorber chamber, the cooling temperature is below the condensation point of the solvent.

The desorbed solvent may be transported into a cooling chamber 10 where it can remain while being cooled.

The chamber in which the adsorber (3) is located may be deaerated after it has been sealed, the deaeration taking place from the air inlet side.

If the desorbed solvent is transported into a cooling chamber for cooling, the desorbed solvent may be circulated obver a refrigeration unit.

The cooling of the desorbed solvent may take place in two steps, a first step wherein it is cooled below the freezing point of the solvnet and, during the increase in temperature of the adsorber, it is cooled to a temperature below the condensation point of the solvent.

The negative pressure applied to the adsorber chamber may fall below the value of 1 mbar.

I claim:

1. A process for the recovery of solvents of a group consisting of trichloroethylene, perchloroethylene and trichloroethane adsorbed in an adsorber comprising the steps:
    (a) heating the adsorber in an adsorber chamber to a temperature which is below the decomposition temperature of the solvent,
    (b) sealing the adsorber chamber off from the surroundings,
    (c) applying a high negative pressure below the value of 10 mbar to the adsorber chamber,
    (d) drawing the desorbed solvent off from the adsorber chamber,
    (e) condensing the desorbed solvent by cooling at a suitable pressure, and
    (f) increasing the temperature of the adsorber to above the decomposition temperature of the solvent (at normal atmospheric pressure) for an effective period during at least a portion of the time when said high negative pressure is applied to the adsorber chamber whereby undercomposed solvent is recovered.

2. A process as defined in claim 1, in which the cooling of the desorbed solvent in step (e) takes place in two steps, whereby it is cooled below the freezing point of the solvent, and during the increase in temperature of the adsorber in step (f), it is cooled to a temperature below the condensation point of the solvent.

3. A process as defined in claim 1, including the step of transporting the desorbed solvent into a cooling chamber, where it remains while being cooled in step (e).

4. A process as defined in claim 2, including the step of transporting the desorbed solvent into a cooling chamber, where it remains while being cooled in step (e).

5. A process as defined in claim 1, including the step of de-aerating the adsorber chamber after it has been sealed, the de-aeration taking place from an air inlet side of the chamber.

6. A process as defined in claim 2, including the step of de-aerating the adsorber chamber after it has been sealed, the de-aeration taking place from an air inlet.

7. A process as defined in claim 3, in which the desorbed solvent in the cooling chamber is circulated over a refrigeration unit.

8. A process as defined in claim 1, in which the cooling of the desorbed solvent in step (e) takes place in two steps, whereby it is cooled below the condensation temperature of the solvent in the first step and below the solidification point of the desorbed solvent in the second step.

9. A process as defined in claim 6, in which the cooling of the desorbed solvent in step (e) takes place in two steps, whereby it is cooled below the condensation temperature of the solvent in the first step and below the solidification point of the desorbed solvent in the second step.

10. A process as defined in claim 1, in which the negative pressure applied to the adsorber chamber falls below the value of 1 mbar.

11. A process as defined in claim 6, in which the negative pressure applied to the adsorber chamber falls below the value of 1 mbar.

12. A process as defined in claim 3, including the step of de-aerating the adsorber chamber after it has been sealed, the de-aeration taking place from an air inlet.

* * * * *